United States Patent
Yamashita et al.

(10) Patent No.: US 8,920,166 B2
(45) Date of Patent: Dec. 30, 2014

(54) ROOT CANAL LENGTH MEASURING APPARATUS AND ROOT CANAL THERAPY APPARATUS

(75) Inventors: Seiichiro Yamashita, Kyoto (JP); Hiroaki Kusakabe, Kyoto (JP); Kazunari Matoba, Kyoto (JP); Tetsuzo Ito, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 668 days.

(21) Appl. No.: 12/075,714

(22) Filed: Mar. 13, 2008

(65) Prior Publication Data

US 2008/0241783 A1 Oct. 2, 2008

(30) Foreign Application Priority Data

Mar. 16, 2007 (JP) ................. 2007-068512

(51) Int. Cl.
A61C 19/04 (2006.01)
(52) U.S. Cl.
CPC .............. *A61C 19/041* (2013.01); *A61C 19/042* (2013.01)
USPC ................. 433/27; 433/72; 600/590; 600/547
(58) Field of Classification Search
CPC ........................... A61C 19/041; A61C 19/042
USPC ............................... 600/590, 547; 433/27, 72
See application file for complete search history.

(56) References Cited

U.S. PATENT DOCUMENTS

| | | | | |
|---|---|---|---|---|
| 5,096,419 A | * | 3/1992 | Kobayashi et al. | 433/72 |
| 5,211,556 A | * | 5/1993 | Kobayashi et al. | 433/72 |
| 5,211,558 A | * | 5/1993 | Bailey et al. | 433/77 |
| 5,295,833 A | * | 3/1994 | Chihiro et al. | 433/224 |
| 5,759,159 A | * | 6/1998 | Masreliez | 600/547 |
| 5,902,105 A | * | 5/1999 | Uejima et al. | 433/27 |
| 6,221,031 B1 | * | 4/2001 | Heraud | 600/590 |
| 6,425,875 B1 | * | 7/2002 | Reifman et al. | 600/590 |
| 2003/0044755 A1 | * | 3/2003 | Jensen | 433/215 |
| 2003/0135127 A1 | * | 7/2003 | Sackner et al. | 600/536 |
| 2004/0158169 A1 | * | 8/2004 | Lewallen et al. | 600/547 |
| 2004/0225234 A1 | * | 11/2004 | Siemons | 600/590 |
| 2006/0154209 A1 | * | 7/2006 | Hayman et al. | 433/215 |
| 2006/0167367 A1 | * | 7/2006 | Stanczak et al. | 600/523 |
| 2006/0184061 A1 | * | 8/2006 | Berger et al. | 600/554 |

(Continued)

FOREIGN PATENT DOCUMENTS

| | | |
|---|---|---|
| DE | 41 39 424 C | 7/1997 |
| DE | 42 32 487 C | 9/1997 |

(Continued)

*Primary Examiner* — Sean Dougherty
*Assistant Examiner* — Michael C Stout
(74) *Attorney, Agent, or Firm* — DLA Piper LLP (US)

(57) ABSTRACT

The present invention provides a root canal length measuring apparatus and a root canal treatment apparatus which can acquire a position of a measurement electrode with high reproducibility in the same root canal. The root canal length measuring apparatus includes a measurement electrode which is inserted into a root canal, an oral electrode which is held in an oral cavity, a measuring section which applies an electric measuring signal between the measurement electrode and the oral electrode and specifies an apex position so as to measure a root canal length, a memory means which stores position data corresponding to a position of the measurement electrode in a root canal acquired by the measuring section, and an operating means which instructs the memory means to store the position data.

18 Claims, 17 Drawing Sheets

(56) References Cited

U.S. PATENT DOCUMENTS

| | | | |
|---|---|---|---|
| 2006/0286511 A1* | 12/2006 | Aleksandrovskiy et al. | 433/215 |
| 2007/0298368 A1* | 12/2007 | Nam | 433/25 |
| 2008/0182223 A1* | 7/2008 | Yamashita et al. | 433/32 |
| 2008/0187880 A1* | 8/2008 | Becker et al. | 433/25 |
| 2008/0255432 A1* | 10/2008 | Nielsen et al. | 600/301 |
| 2009/0221931 A1* | 9/2009 | Crohn et al. | 600/547 |

FOREIGN PATENT DOCUMENTS

| | | | | |
|---|---|---|---|---|
| DE | 198 54 223 C | | 5/2001 | |
| DE | 195 20 765 B | | 7/2004 | |
| JP | S59-36319 | | 3/1984 | |
| JP | H4-64354 A | | 2/1992 | |
| JP | H4-73055 A | | 3/1992 | |
| JP | H5-192356 A | | 8/1993 | |
| JP | H10-155818 A | | 6/1998 | |
| JP | 3113095 | | 11/2000 | |
| JP | 2002-509455 A | | 3/2002 | |
| JP | 2003-199770 A | | 7/2003 | |
| WO | WO-2005/115271 | * | 12/2005 | A61C 19/04 |
| WO | WO-2007/057878 | * | 5/2007 | A61C 19/04 |

* cited by examiner

F I G. 3
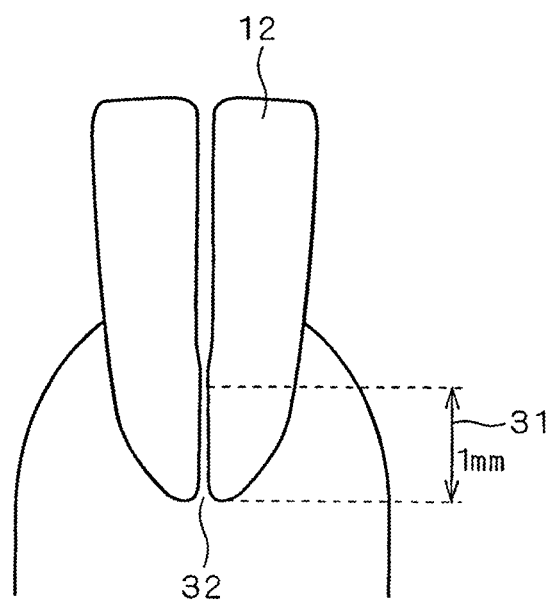

F I G . 4 A
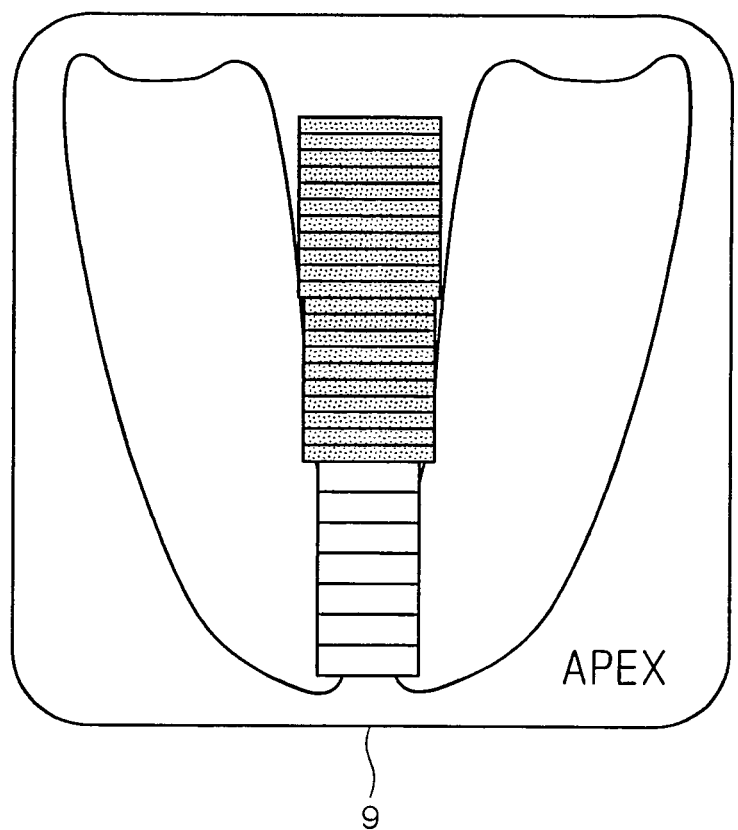
F I G . 4 B
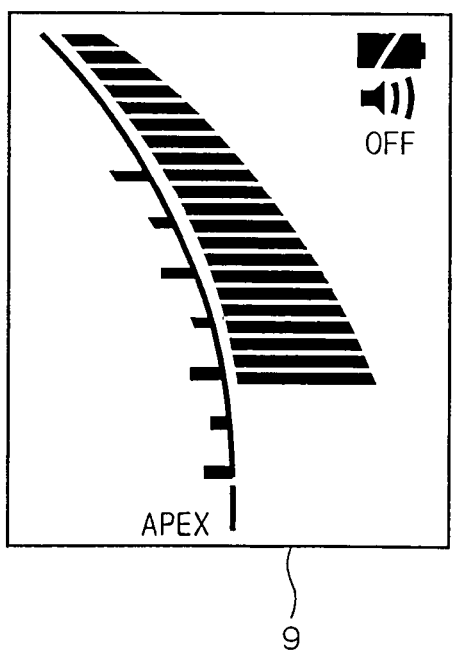

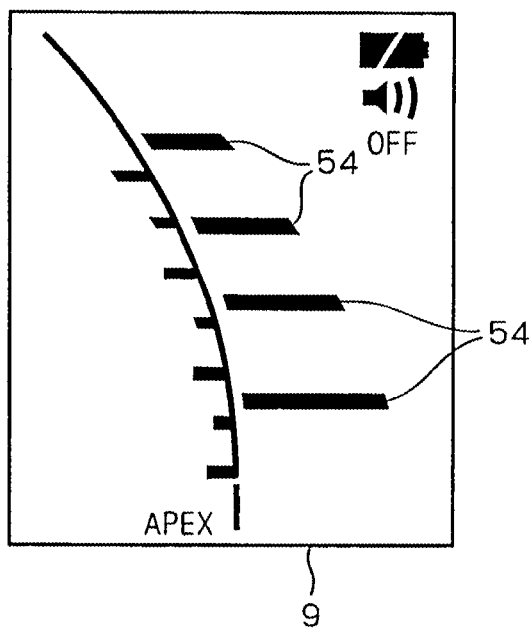

F I G . 8
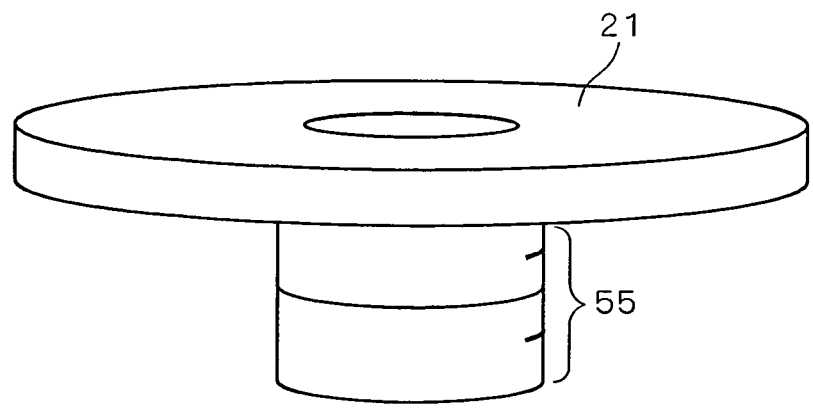

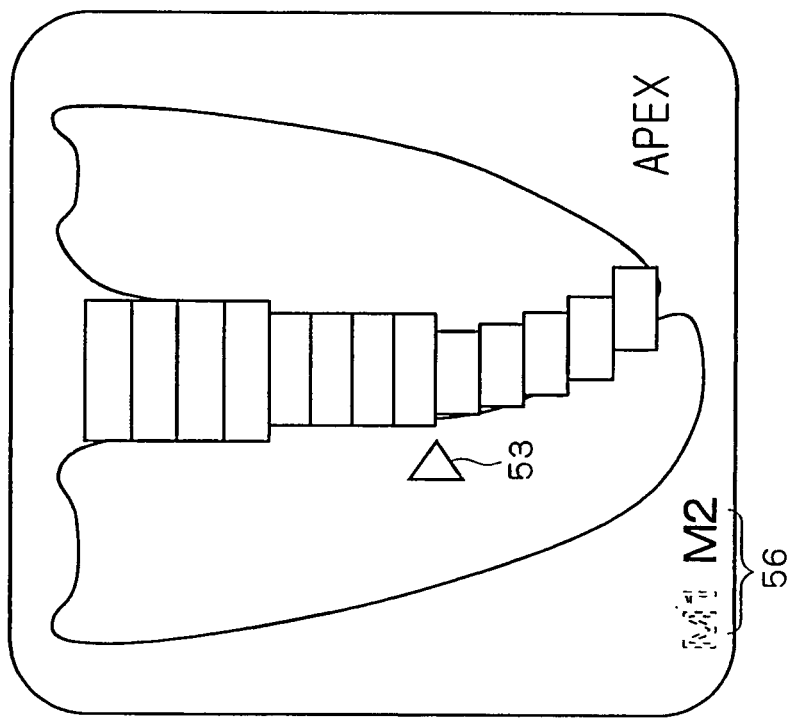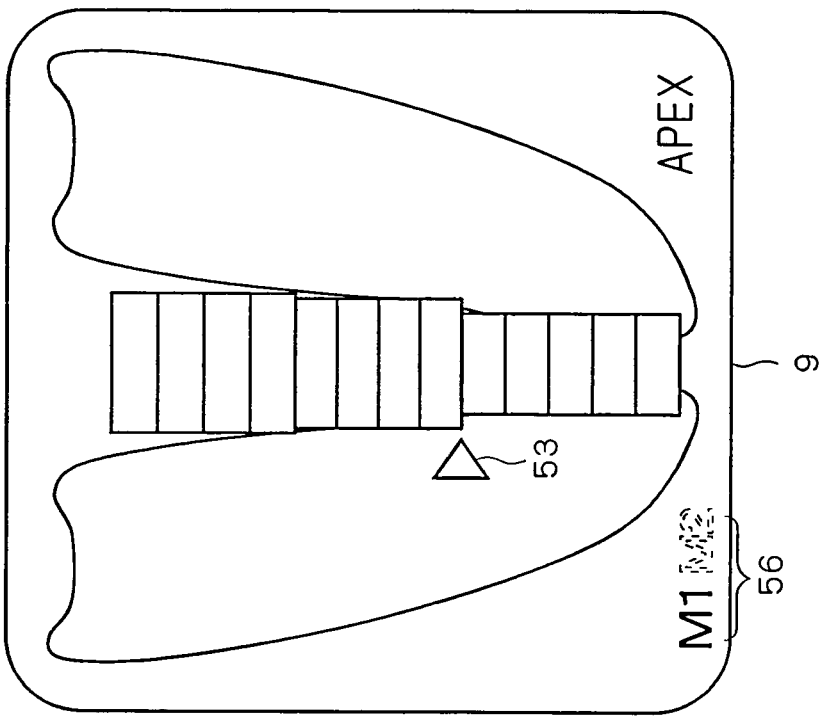

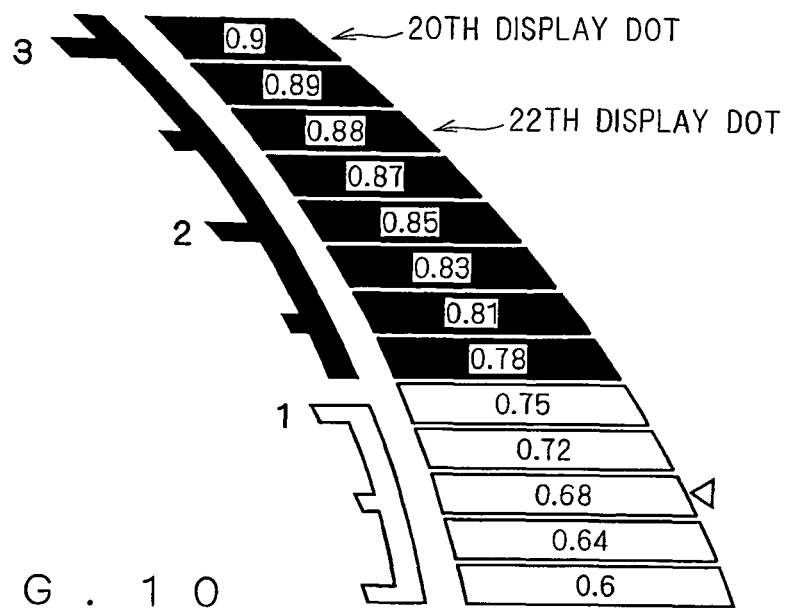
F I G. 1 0
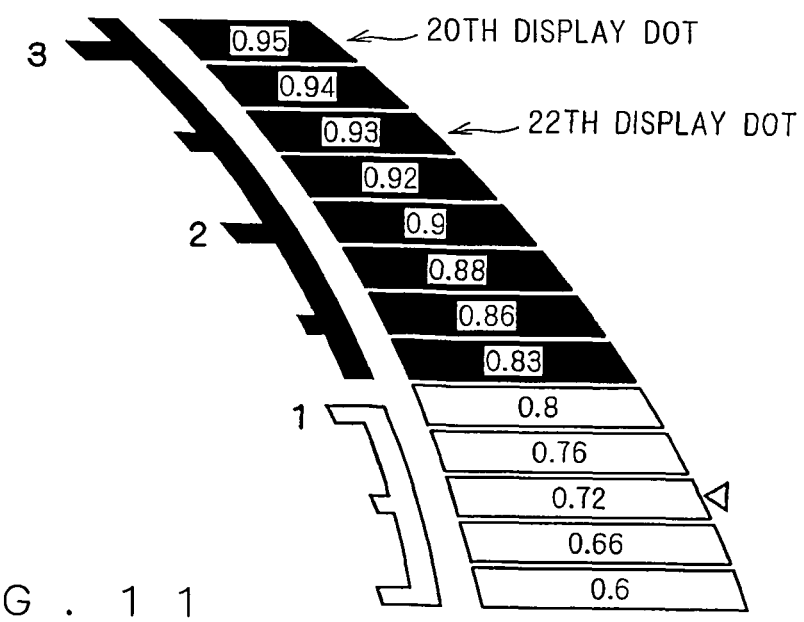
F I G. 1 1

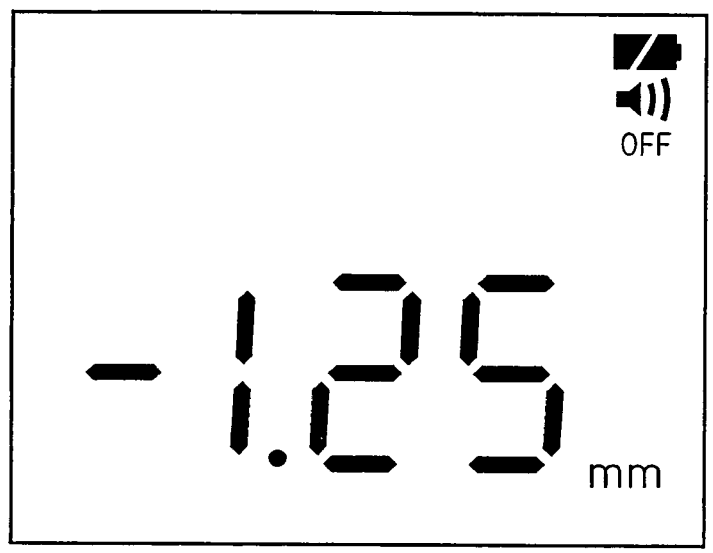
F I G . 1 2

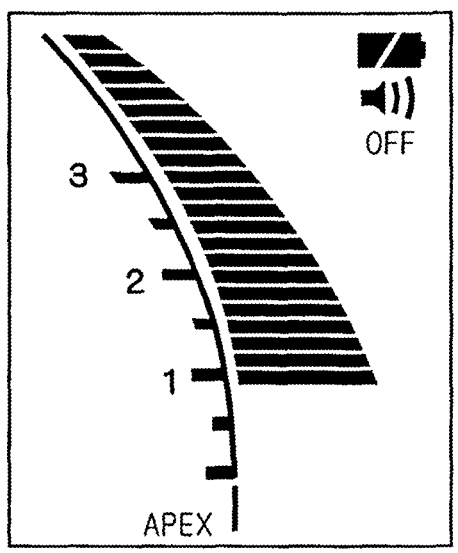
F I G . 1 9

ROOT CANAL LENGTH MEASURING APPARATUS AND ROOT CANAL THERAPY APPARATUS

BACKGROUND OF THE INVENTION

1. Field of the Invention

The present invention relates to a root canal length measuring apparatus and a root canal treatment apparatus which are used for dental treatment and diagnosis.

2. Description of the Background Art

As shown in FIG. 16, a human tooth is composed of an enamel 101, a dentin 102 and a cementum 103. The tooth is supported by an alveolar bone 104 and a gum 105. A dental pulp 106 is present inside the tooth, and blood vessels and nerves pass from the dental pulp 106 through a root canal 107 so as to be connected to blood vessels below the alveolar bone 104. Ends of the root canal 107 on side of the alveolar bones 104 are called as an apex 108.

A root membrane 109 is present on a boundary between a tooth root of the cementum 103 including the apex 108 and the alveolar bone 104. The root membrane 109 is a membrane which covers the entire tooth root of the tooth 101 as shown in FIG. 17. As shown in FIG. 17, the root canal has a portion which is called as an apical constriction 111 where the root canal becomes narrow near a lower portion 110 of the tooth. A shape of the apical constriction 111 varies between individuals, namely, some are curved and some are straight as shown in FIG. 17. In FIG. 17, an opening of the root canal on the robot membrane 109 side is called as an apical foramen 112.

In general, root canal treatment using a root canal length measuring apparatus and a root canal treatment apparatus is done in the following manner. A length of a root canal to be measured or treated is measured. The root canal is enlarged based on a result obtained by the measurement. Thereafter, the enlarged root canal is cleaned, and the enlarged root canal is filled with a predetermined material.

Specifically, in the root canal length measurement, as shown in FIG. 18, a measurement electrode 201 of a thin file (tool having diameter of 0.10 mm to 0.15 mm for enlarging a root canal) is inserted into a root canal 203 of a tooth 202, and an electric measuring signal is applied between the measurement electrode 201 and an oral electrode 204, so that an apex 205 is detected. After the apex 205 is detected, a working length is determined based on a position of the apex 205.

The method for applying the electric measuring signal between the measurement electrode 201 and the oral electrode 204 so as to detect the apex 205 includes a method using a change in impedance in the root canal as described below. When the measurement electrode 201 is in the position of the apex 205, the impedance value in the root canal is directly used based on a principle that an impedance value between the measurement electrode 201 and an oral mucosa becomes constant. In this method, however, the position of the apex 205 is a position where the measurement electrode 201 passes through an apical foramen 112 and comes in contact with the root membrane 109 as shown in FIG. 17.

There is also a method in which when the measurement electrode 201 is in the position of the apex 205, the apex is detected by using a difference in the impedance in the root canal based on a principle that a difference in the impedance in the root canal measured at two or more kinds of frequencies becomes constant. This method, however, occasionally requires such adjustment that the impedance value in the root canal is added to a difference in the impedance in the root canal.

When the measurement electrode 201 is on the position of the apex 205, the apex is detected by using a ratio of the impedance in the root canal based on a principle that the ratio of the impedance in the root canal measured at two or more kinds of frequencies becomes constant.

Besides the above methods, there is a method in which the ratio or the difference is not obtained, the apex is detected according to a calculating table which is prepared in advance where the impedance in the root canal measured at two or more kinds of frequencies is used as a pointer. The principle of this method is similar to those of the methods for obtaining the ratio and difference in the impedance in a root canal.

In the above methods, as shown in FIG. 18, a change in a measurement current flowing in a root canal is measured by a detecting resistor 206, so that the impedance in the root canal is obtained. In this technical field, the measurement of the impedance in a root canal is not limited to the direct measurement of the impedance, and thus includes measurement of an amount corresponding to the impedance. That is to say, measurement of a current value or a voltage value corresponding to the impedance is also included in the measurement of the impedance in a root canal. The above describes the apex detecting methods according to the measurement of the impedance in a root canal, but beside them, a method for detecting a change in a phase of an electric current or detecting a change in current density so as to detect an apex is occasionally adopted.

In the root canal enlargement, the file is gradually thickened to a position, which is 0.5 to 2 mm away from the apex detected by the root canal length measurement toward a tooth crown 207 side, as a reference position, so that the root canal is enlarged. Specifically, a root canal is enlarged by, for example, a step back method for enlarging the root canal up to a position 0.5 mm away from the apex using a file #20 (diameter: 0.2 mm), and up to a position 1.0 mm away from the apex using a file #30 (diameter: 0.3 mm), and up to a position 2.0 mm away from the apex using a file #40 (diameter: 0.4 mm).

In the root canal cleaning, contaminants in the enlarged root canal and chips generated at the time of the enlargement are rinsed. In the root canal filling, the root canal is filled with a predetermined substance so that the cleaned root canal is not reinfected.

A conventional root canal length measuring apparatus does not measure a root canal length itself but detects a position of the apex 205 shown in FIG. 18. For this reason, the conventional root canal length measuring apparatus has only a function for detecting the apex 205 but does not have a function for displaying to what extent a position of a tip of the measurement electrode 201 is away from the apex 205.

An indicator of a root canal length measuring apparatus described in Japanese Patent No. 3113095 shows arrival of the tip of the measurement electrode at the apex 205 by means of apex display as shown in FIG. 19. In FIG. 19, however, besides the apex display, a change in the measurement electrode position in the root canal can be displayed only as a guide. Scale marks 1 to 3 are given to the guide display, but this display does not show a distance from the apex 205 in the on-measuring root canal to the measurement electrode 201.

The feature of the root canal as one of human tissues is not constant because a shape of a root canal and an environment in a root canal varies. For this reason, the root canal measuring apparatus described in Japanese Patent No. 3113095 enables accurately reading from the indicator only whether or not the tip of the measurement electrode 201 has arrived at the apex 205 and whether the tip of the measurement electrode 201 is coming close to or is moving away from the apex 205.

As described in the background of the invention, the conventional root canal length measuring apparatus and the root canal treatment apparatus can accurately detect only the position of an apex. When the root canal treatment such as the root canal enlargement is done, however, it is occasionally necessary to accurately acquire positions in the root canal other than the apex. Particularly, it is important for the root canal treatment to knows a distance from the apex as a reference position at the time of the root canal enlargement, the position of the apical constriction, the position of the curved portion of the root canal, a position where pathologic changes such as breakage of a collateral, a perforated portion and a tooth root occur, and a position of a treatment difficult portion such as a step and a ledge.

In the case of the canal root enlargement treatment using a motor, in general, a motor driving method is changed on predetermined positions. In such a constitution, for example, the rotating speed of the motor per hour is reduced on a portion where the root canal is curved, and the motor is rotated reversely near an apex. For this reason, it is important to know the above positions with high reproducibility in the same root canal.

SUMMARY OF THE INVENTION

It is an object of the present invention to provide a root canal length measuring apparatus and a root canal treatment apparatus which can acquire a position of a measurement electrode with high reproducibility in the same root canal.

The present invention is a root canal length measuring apparatus which has a measurement electrode, an oral electrode, a measuring section, a memory means and an operating means. The measurement electrode is inserted into a root canal. The oral electrode is held in an oral cavity. The measuring section applies an electric measuring signal between the measurement electrode and the oral electrode and specifies an apex position so as to measure a root canal length. The memory means stores position data corresponding to a position of the measurement electrode in the root canal acquired by the measuring section. The operating means instructs the memory means to store the position data.

The root canal length measuring apparatus of the present invention has the memory means which stores position data corresponding to the position of the measurement electrode and the operating means which instructs the memory means to store the position data. For this reason, the stored position data can be acquired with high reproducibility in the same root canal.

The present invention is a root canal length measuring apparatus has a measurement electrode, an oral electrode, a display section, a memory means and an operating means. The measurement electrode is inserted into a root canal. The oral electrode is held in an oral cavity. The measuring section applies an electric measuring signal between the measurement electrode and the oral electrode and specifies an apex position so as to measure a root canal length. The display section displays display data corresponding to a position of the measurement electrode in the root canal based on a value obtained from the measuring section. The memory means stores the display data. The operating means instructs the memory means to store the display data.

The root canal length measuring apparatus of the present invention has the memory means which stores display data and the operating means which instructs the memory means to store the display data. For this reason, a positional relationship between the position of the measurement electrode in the same root canal and the stored position data stored can be acquired with high reproducibility.

The present invention is a root canal treatment apparatus which has the root canal length measuring apparatus, a root canal treatment tool having a function of the measurement electrode and treats a root canal, a driving section for driving the root canal treatment tool, and a control section for controlling the driving section based on the position data or the display data stored in the memory means.

The root canal treatment apparatus of the present invention can control the driving section on a desired position of the measurement electrode with high reproducibility in the same root canal, and can do the root canal treatment easily and accurately. In the root canal treatment apparatus, the root canal treatment tool for the root canal treatment can serve also as the measurement electrode for the root canal length measurement. For this reason, a complicated operation for replacing the electrode and tool is not required, and the measurement of the root canal length and the root canal treatment can be made simultaneously, namely, this apparatus is convenient.

These and other objects, features, aspects and advantages of the present invention will become more apparent from the following detailed description of the present invention when taken in conjunction with the accompanying drawings.

BRIEF DESCRIPTION OF THE DRAWINGS

FIG. 3 is a diagram explaining an apical constriction of root canal;

FIGS. 4A and 4B are diagrams illustrating display examples of the root canal length measuring apparatus according to the first embodiment of the present invention;

FIG. 6 is a display example of the root canal length measuring apparatus according to a second embodiment of the present invention;

FIG. 8 is a schematic diagram illustrating a stopper of the root canal length measuring apparatus according to the second embodiment of the present invention;

FIGS. 9A and 9B are diagrams illustrating another display examples of the root canal length measuring apparatus according to the second embodiment of the present invention;

FIG. 10 is a diagram illustrating a display example of a conventional root canal length measuring apparatus;

FIG. 11 is a diagram illustrating a display example of the root canal length measuring apparatus according to a third embodiment of the present invention;

FIG. 12 is a diagram illustrating another display example of the root canal length measuring apparatus according to the third embodiment of the present invention;

FIG. 19 is a diagram illustrating a display example of the conventional root canal length measuring apparatus.

DESCRIPTION OF THE PREFERRED EMBODIMENTS

Outline

Figure 1:
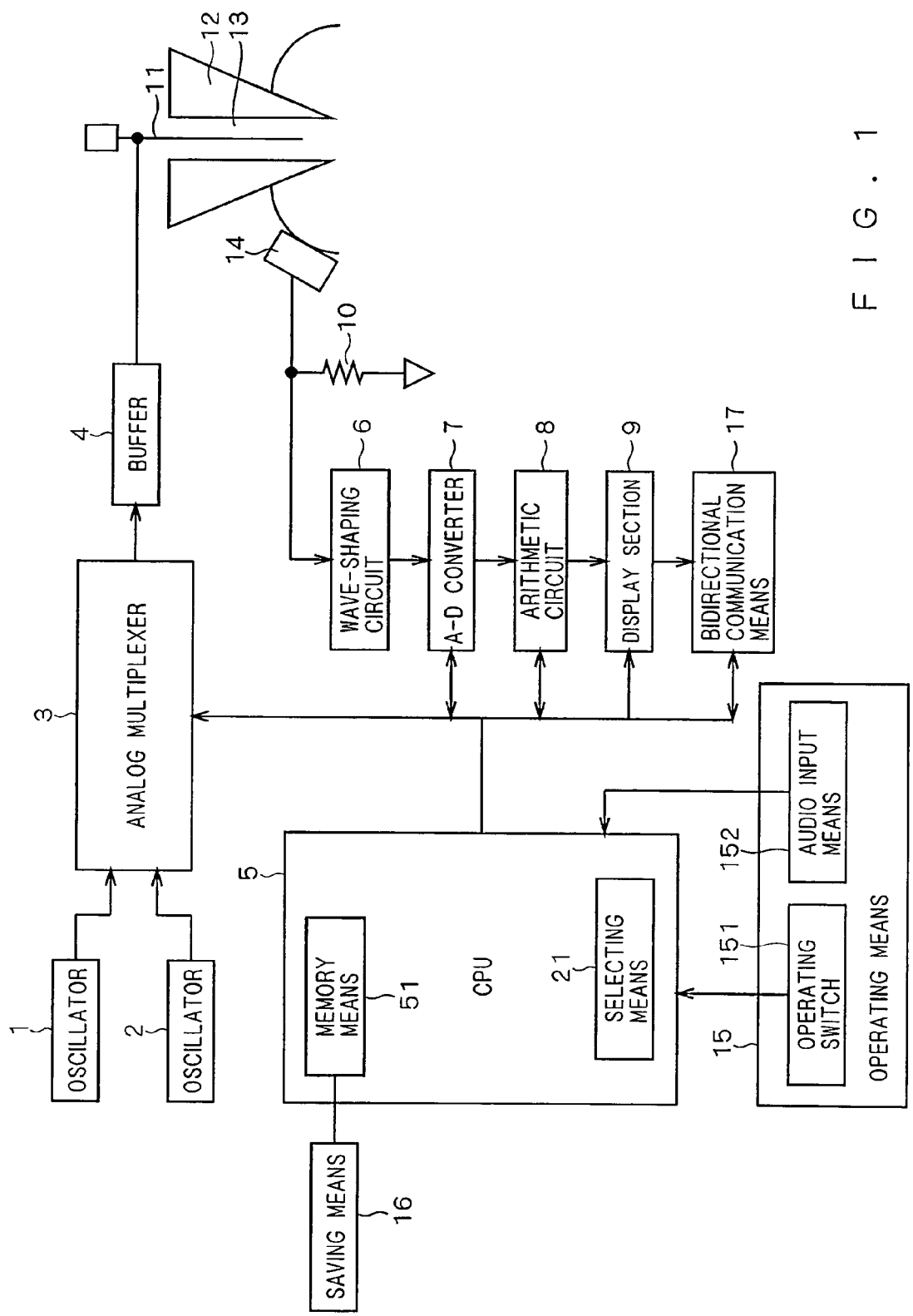
FIG. 1 is a block diagram illustrating a root canal length measuring apparatus according to a first embodiment of the present invention.

A conventional root canal measuring apparatus has a single-function for detecting an apex position as described in the background of the invention. However, the root canal measuring apparatus of the present invention can accurately acquire a reference position of a measurement electrode in a root canal which is necessary for whole root canal treatment such as root canal enlargement, root canal cleaning and root canal filling with high reproducibility unlike the conventional root canal length measuring apparatus.

Specifically, the root canal length measuring apparatus of the present invention includes a memory means and an operating section. The memory means stores position data such as an impedance value corresponding to a position of the measurement electrode therein in the position of the measurement electrode in the root canal which is desired to be stored in the measuring apparatus by an operator. The operating section instructs the position data which is desired to be stored by the operator. The position data is data corresponding to the position of the measurement electrode in the root canal acquired by a measuring section. Such data includes an impedance value itself in the root canal, a difference in the impedance value and a ratio of the impedance value. The root canal length measuring apparatus of the present invention may store display data displayed on a display section correspondingly to the position of the measurement electrode in the root canal instead of the position data. The display data is data displayed on the display section based on a value measured by the measuring section of the root canal length measuring apparatus. Specifically, the display data includes number of display dots in an indicator shown in FIG. 19 (an amount showing nth display dot).

In the root canal length measuring apparatus of the present invention, the operator may pull up the measurement electrode towards a tooth crown side from an apex position (display position of APEX) by a predetermined distance, so that position data in that position or the display data may be stored. At the time of the root canal treatment, treatment such as enlargement of a root canal is done by the root canal treatment apparatus based on the position of the stored position data or the display data.

In the conventional root canal length measuring apparatus, an accurate position cannot be detected in portions other than the apex essentially as described in the background of the invention. In the root canal length measuring apparatus of the present invention, however, since reproducibility of the position data or the display data is high on any position in the same root canal, the memory means and the operating means are provided so as to store the position data or the display data on any position and specify the position in the root canal. That is to say, in the root canal length measuring apparatus of the present invention, the positions of the measurement electrode showing the same position data or the same display data in the same root canal are substantially accurately the same positions, but the same position data or the same display data in a different root canal show different positions in the root canal. Such a principle is utilized in the present invention.

The root canal length measuring apparatus of the present invention sequentially stores position data or display data on positions where the measurement electrode in the apex position is pulled out by any length (distance), so as to be capable of measuring the distance from the apex accurately. For example, the position data or the display data are stored while the measurement electrode is being pulled up by 1 mm, 2 mm and 3 mm sequentially. In this case, when the measurement electrode is again inserted into the same root canal, regarding the positions showing the stored position data or display data, the distance from the apex can be accurately obtained.

When an environment in the root canal changes at the time of the root canal enlargement and a thickness of a file changes, an error is generated, but the error in the same root canal is smaller than an error due to a variation between root canals. For this reason, in the root canal length measuring apparatus of the present invention, the positions of the measurement electrode or the file serving also as the measurement electrode in a root canal can be measured more accurately than the conventional root canal length measuring apparatuses, and thus the accurate treatment is enabled.

First Embodiment

FIG. 1 is a block diagram illustrating the root canal length measuring apparatus according to the first embodiment. The root canal length measuring apparatus shown in FIG. 1 has an oscillator 1 which outputs a measuring signal having a predetermined frequency, and an oscillator 2 which outputs a measuring signal having a frequency different from the oscillator 1. Further, the root canal length measuring apparatus shown in FIG. 1 has an analog multiplexer 3, a buffer 4 and a CPU 5. The root canal length measuring apparatus shown in FIG. 1 further has a wave-shaping circuit 6, an A-D converter 7, an arithmetic circuit 8, a display section 9 and a detecting resistor 10.

In the root canal length measuring apparatus shown in FIG. 1, a measurement electrode 11 connected to the buffer 4 is inserted into a root canal 13 of a tooth 12, and a change in impedance in the root canal between an oral electrode 14 connected to the detecting resistor 10 and the measurement electrode 11 is measured. The CPU 5 controls operation timing of the respective circuits, and changes outputs from the oscillators 1 and 2 by every 10 msec, for example, via the analog multiplexer 3. The output from the analog multiplexer 3 is applied to the measurement electrode 11 via the buffer 4.

In the root canal length measuring apparatus, shown in FIG. 1, the oscillators 1 and 2, the analog multiplexer 3, the buffer 4, the CPU 5, the wave-shaping circuit 6, the A-D converter 7, the arithmetic circuit 8 and the detecting resistor 10 compose a measuring section which measures a change in the impedance in a root canal. In this measuring section, the change in the impedance between the measurement electrode 11 and the oral electrode 14 is detected as a measurement current in the detecting resistor 10, and the measurement current is rectified by the wave-shaping circuit 6 so that the waveform is shaped. Thereafter, the measurement current is converted into digital data by the A-D converter 7. The arithmetic circuit 8 successively latches the digital data from the A-D converter 7 so as to perform a predetermined operation.

The measuring section shown in FIG. 1 measures the change in the impedance value between the measurement electrode 11 and the oral electrode 14, but the present invention is not limited to this. All the measuring section of the present invention has to have is a function for applying an electric measuring signal between the measurement electrode 11 and the oral electrode 14 so as to measure a root canal length, and a function for changing position data according to positions of the measurement electrode 11 in a root canal. The apex position may be detected in the measuring section by measuring current density or the like other than the change in the impedance.

In the root canal length measuring apparatus according to the first embodiment, a memory means 51 is provided into the CPU 5 as shown in FIG. 1. The memory means 51 stores position data such as impedance in a root canal and display data such as display dots on the display section 9 therein. The root canal length measuring apparatus according to the first embodiment includes an operating means 15 as shown in FIG. 1, and the operating means 15 instructs the CPU 5 to store the position data or the display data in the memory means 51. The operating means 15 includes an operating switch 151 such as a switch or a foot pedal mounted to a case of the root canal length measuring apparatus, or an audio input means 152 which senses an audio so as to perform an operation. A plurality of means may be combined.

Figure 2:
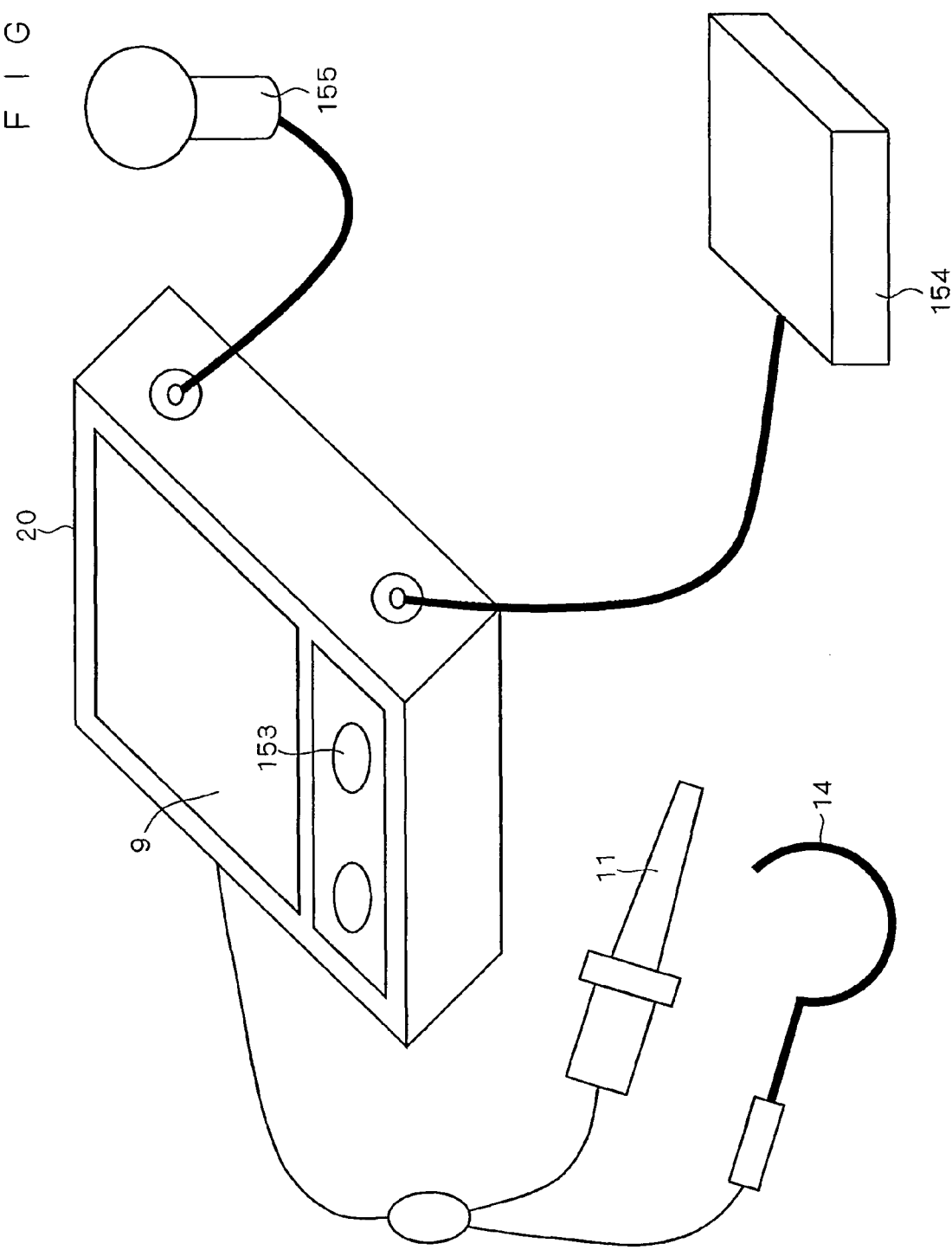
FIG. 2 is a schematic diagram illustrating the root canal length measuring apparatus according to the first embodiment of the present invention.

FIG. 2 is an outline schematic diagram illustrating the root canal length measuring apparatus according to the first embodiment. The root canal length measuring apparatus 20 shown in FIG. 2 has the measurement electrode 11 and the oral electrode 14 for measuring the change in the impedance in a root canal, and an operating button 153, the foot pedal 154 and a microphone 155 as the operating means 15. For this reason, an operator who uses the root canal length measuring apparatus shown in FIG. 2 operates any one of the operating button 153 provided near the display section 9, the foot pedal 154 positioned around operator's feet and the microphone 155 mounted near an operator's chest, so that position data or display data can be stored in the memory means 51.

The root canal length measuring apparatus according to the first embodiment has a saving means 16 as shown in FIG. 1, and the saving means 16 can save the position data or the display data stored in the memory means 51. A nonvolatile storage medium such as an HDD or a flash memory is used in the saving means 16. The saving means 16, which has a detachable storage medium, enables reading and using previous data only by inserting a storage medium necessary for retreatment into a predetermined portion of the root canal length measuring apparatus according to the first embodiment.

The saving means 16 saves the position data or the display data stored in the memory means 51 together with management number therein, and the operator easily reads the saved position data or display data based on the management number. As the management number, for example, a number obtained by combining a patient's number and positions of a tooth and a root canal is used. The management number (discrimination code) is automatically updated every time when new root canal position data is stored. For this reason, the management number is written on a medical chart so that the remeasurement of the root canal length is not necessary and the efficient root canal treatment is enabled. Needless to say, a system for updating the management number per patient may be adopted. When 0 is input as the management number, a display property may be automatically changed into one set at the factory.

Figure 17:
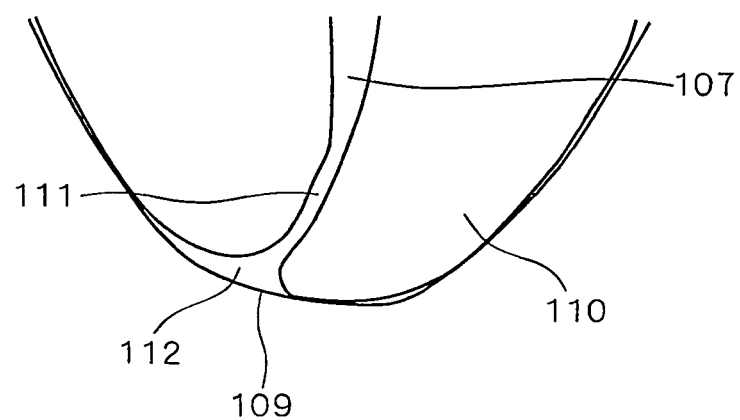
FIG. 17 is a cross-sectional view illustrating a lower portion of the tooth.
Figure 18:
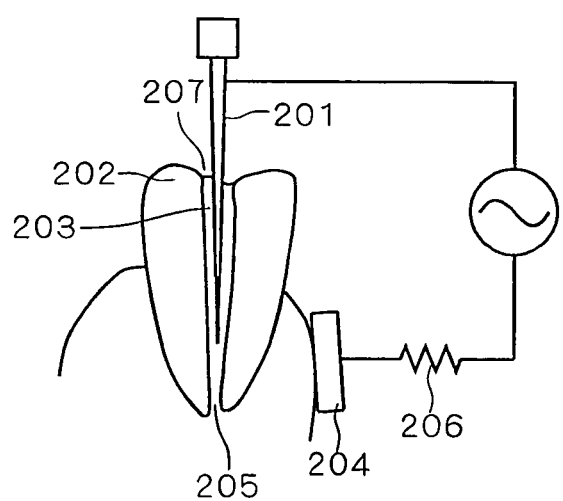
FIG. 18 is a pattern diagram illustrating a conventional root canal length measuring apparatus.

The root canal length measuring apparatus according to the first embodiment has a bidirectional communication means 17 as shown in FIG. 17, and the bidirectional communication means 17 can transmit and receive the position data or the display data stored in the memory means 51 to and from the external devices such as a personal computer (PC), another root canal measuring apparatus and a root canal treatment apparatus. The provision of the bidirectional communication means 17 enables the position data or the display data stored in the memory means 51 to be transmitted to PC and to be transmitted/received to/from the same kind of apparatuses. The bidirectional communication means 17 may be wired or wireless. When the bidirectional communication means 17 transmits data to PC, a management number is given to the data.

The root canal length measuring apparatus according to the first embodiment has the display section 9 as shown in FIG. 1, but the display section 9 does not have to be necessarily provided in the present invention. Measured data may be displayed on an external display means connected by the bidirectional communication means 17.

An operation for storing the position of an apical constriction as a reference position using the root canal length measuring apparatus according to the first embodiment is described below. Since the apical constriction is a typical reference position when the treatment such as the root canal enlargement is done, when the reference position can be measured with high reproducibility, there are advantages that the treatment can be done quickly, or the like. In the first embodiment, examples where the position of the apical constriction is the reference position are described, but the reference position, which is measured by the root canal length measuring apparatus of the present invention, is not limited to the position of the apical constriction. For example, a position where the root canal starts to be curved, or a position where a pathologic change such as collateral of the root canal, trephination portion or root breakage are present may be stored as the reference position.

FIG. 3 is a cross-sectional view illustrating the tooth 12 having the apical constriction 31. The apical constriction 31 shown in FIG. 3 is present up to a position about −1 mm away from the apex 32. Normally the root canal length measuring apparatus cannot electrically acquire whether the root canal is constricted or not, but when an operator who inserts the measurement electrode 11 into the root canal is a skilled hand, the operator occasionally senses with the operator's fingers whether the root canal is constricted or not. In this case, with the root canal length measuring apparatus according to the first embodiment, the operator can store the position data or the display data on that position as the reference position.

FIGS. 4A and 4B illustrate display states of the indicator when the operator senses with the operator's fingers that the root canal is constricted at the time of the root canal length measurement. FIG. 4A is a pattern diagram of the root canal illustrating a display example that a change in the impedance value in the root canal is displayed by lighting of display dots, and FIG. 4B illustrates a display example of the general root canal length measuring apparatus. In the root canal length measuring apparatus according to the first embodiment, the operating means 15 such as the foot pedal is operated on the positions shown in FIGS. 4A and 4B, and the position data or the display data is stored in the root canal length measuring apparatus. After the root canal length measurement is continued and the apex position is detected, the measurement electrode 11 is pulled out of the root canal.

Figure 5A:
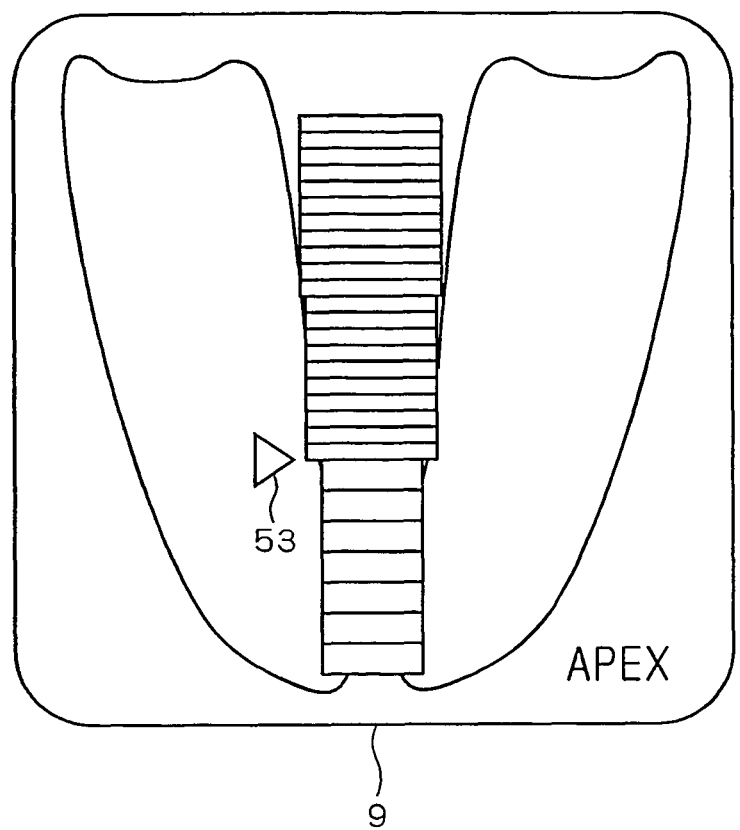
FIGS. 5A and 5B are display examples of the root canal length measuring apparatus according to the first embodiment of the present invention.
Figure 5B:
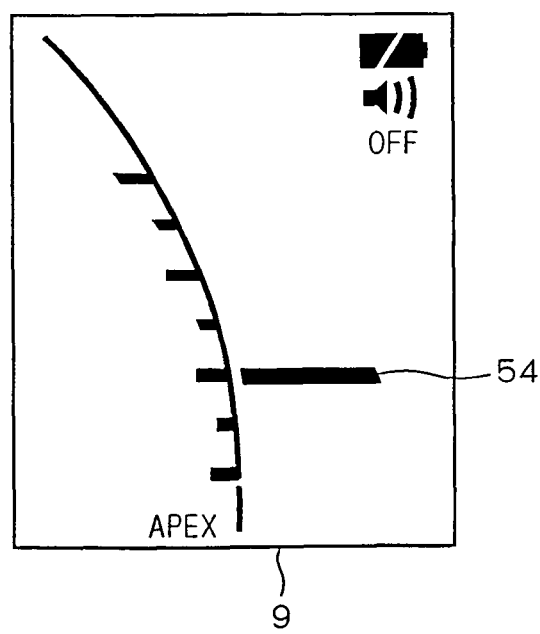

In the root canal length measuring apparatus according to the first embodiment, the displays after the measurement electrode 11 is pulled out of the root canal are as shown in FIGS. 5A and 5B. In FIG. 5A, the operating means 15 is operated, and a storage position mark 53 is displayed on the display position of the position data or the display data stored in the root canal length measuring apparatus. On the other hand, in FIG. 5B, the operating means 15 is operated, and a display dot 54 on the display position of the position data or the display data stored in the root canal length measuring apparatus is turned on. The position of the storage position mark 53 displayed in FIG. 5A or the display dot 54 displayed in FIG. 5B shows the position of the apical constriction 31 detected in the measured root canal by the operator.

When the treatment such as the root canal enlargement is done, the storage position mark 53 shown in FIG. 5A or the display dot 54 shown in FIG. 5B can be used as an indication of the position of the apical constriction 31.

In the case of the root canal treatment apparatus using a root canal treatment tool (for example, a file or a reamer as a root canal enlargement tool) as the measurement electrode 11 of the root canal length measuring apparatus according to the first embodiment, the operator can very easily get a state in which the tool is coming close to the apical constriction 31, and a state in which the tip of the root canal treatment tool arrives at the apical constriction 31 can be shown accurately. That is to say, when the position of the storage position mark 53 shown in FIG. 5A or the display dot 54 shown in FIG. 5B matches with the display of the indicator, the operator can accurately know that the root canal treatment tool (measurement electrode 11) has arrived at the position of the apical constriction 31. Therefore, the operator may do the treatment such as the root canal enlargement up to the position of the apical constriction 31 shown in FIGS. 5A and 5B.

When the storage position mark 53 shown in FIG. 5A or the display dot 54 shown in FIG. 5B are displayed by blinking, visibility for operators becomes high. Further, when a display color of the storage position mark 53 shown in FIG. 5A or the display dot 54 shown in FIG. 5B is changed, visibility for operators becomes high. The method for expressing the display position of the apical constriction 31 is not limited to the above method. When the measurement electrode 11 arrives at the display position of the apical constriction 31 shown in FIGS. 5A and 5B, an audio warning may be given.

The above description refers to the case where the apical constriction 31 is set as the reference position in the root canal length measuring apparatus according to the first embodiment. The root canal length measuring apparatus of the present invention is not limited to the above embodiment, and also can perform treatment on a curve or the like of a root canal recognizable with the operator's fingers similarly. When the curved portion of a root canal can be accurately gotten, it can be easily known whether or not the root canal treatment tool which serves also as the measurement electrode 11 is near the curved portion at the time of the root canal enlargement. Since the edged tool of the root canal treatment tool (file or reamer) is easily fractured on the curved portion of the root canal, when the curved portion can be accurately acquired, attention about this portion can be invited, and the fracture of the edged tool of the root canal treatment tool can be reduced.

The root canal length measuring apparatus of the present invention can set a position as the reference position to which an attention should be paid due to treatment as a position of an affected area present in a root canal, or an obstructed position in the root canal.

The impedances values in a root canal or values obtained by the impedance values naturally are the same in the same position in the same root canal. Utilizing this principle, the root canal length measuring apparatus of the present invention detects the matching between the impedance in a root canal measured and stored in advance or the value obtained by the impedance and the measured value so as to be capable of specifying the reference position with high reproducibility even when the measurement electrode 11 is on a position other than the apex. For this reason, the operator who has an excellent skill uses the recognized reference position of the apical constriction 31 or the curved portion so that another operator can do the treatment such as the root canal enlargement.

Application examples of the root canal length measuring apparatus of the present invention include a reference position when a warning beep such as buzzer is emitted and a reference position where the expressing method on the display section 9 is changed. Specifically, when the measurement electrode 11 has arrived at the position of the stored position data or the like, a warning beep such as buzzer is emitted or a tone quality is changed, so that the operator can get the position of the measurement electrode 11 without viewing the display section 9. When a clinically important position is set as the reference position and the measurement electrode 11 arrives at the reference position, the display section 9 is switched into a more detailed display which is enlarged.

Second Embodiment

A method for measuring an accurate position from an apex with high reproducibility in the root canal length measuring apparatus according to the second embodiment is described below. In the conventional root canal length measuring apparatus, scale marks 1, 2 and 3 are given to the indicator of the display section. A value indicated by the scale marks is a distance from an apex obtained by an average value of results of measuring the distances from a lot of root canals, and thus these scale marks are given as only guides. For example, even if the display section indicates the scale mark 1, it is not ensured that the measurement electrode is present on a position −1.0 mm away from the apex. As the measurement electrode is moved away from the apex by −2.0 mm and −3.0 mm, its error becomes larger, and thus these scale marks cannot be practically used.

The conventional root canal length measuring apparatus can approximately accurately detect the apex position although the measurement electrode 11 is not correlate with the indicator on places other than the apex. Normally, when the indicator swings to the position shown by APEX, the arrival at the apex is known with high reproducibility. For this reason, in the conventional root canal length measuring apparatus, in general, when the indicator arrives at APEX and the apex position can be detected, the position is located by a stopper and is pulled out of the root canal.

On the other hand, in the root canal length measuring apparatus according to the second embodiment, the operator pulls out the measurement electrode 11 from the position at the time when the indicator arrives at APEX by a predetermined amount, and position data or display data at that time is stored. Specifically, when the measurement electrode 11 is a file with a stopper and the measurement electrode 11 arrives at the apex, the stopper is moved, so that the distance from the tooth crown to the apex is set. Thereafter, the foot pedal or the operating switch is operated on a position where the measurement electrode is pulled out from the apex by about 0.5 mm, and position data or display data on that position is stored. The foot pedal or the operating switch is operated on a position where the measurement electrode is pulled out from the apex by about 1.0 mm, and position data or display data on that position is stored. Similarly, position data or display data on positions where the measurement electrode is pulled out from the apex by about 2.0 mm and 4.0 mm is stored.

Due to the above operations, in the root canal length measuring apparatus according to the second embodiment, the display dots 54 corresponding to the positions −0.5 mm, −1.0 mm, −2.0 mm and −4.0 mm away from the apex are blinked or turned on in the display section 9 as shown in FIG. 6. As a result, the operator can accurately measure the distances from the apex with high reproducibility in the same root canal. For this reason, when the root canal is enlarged at the stage of the treatment after the measurement of the root canal length, the display dots 54 obtained by the above operation are used so that root canal treatment tools suitable for the distances −0.5 mm and −1.0 mm away from the apex are selected, or the root canal treatment tools can be operated with a suitable force. As a result, the treatment of the root canal enlargement can be done accurately.

Specifically, when the indicator arrives at the display dot showing −4.0 mm at the time of the root canal enlargement, the operator can recognize that the root canal treatment tool, which also serves as the measurement electrode 11 (edged tool (file) for the root canal enlargement), is coming close to the apex. When the indicator arrives at the display dot showing −1.0 mm, a rotating direction of a motor for rotating the root canal treatment tool is reversed or the normal rotation and the reverse rotation are repeated. When the indicator arrives at the display dot showing −0.5 mm, a thick root canal treatment tool is not certainly used.

The root canal length measuring apparatus according to the second embodiment stores not only the reference position showing the distance but also the position showing the apical constriction or the curved position and display them, so that more accurate and safe treatment can be done. In the root canal length measuring apparatus according to the second embodiment, since the operator sets and inputs so as to store position data or display data on any position in each root canal to be treated, the reference position (the accurate distance from the apex or the position of the apical constriction) in the same canal can be recognized accurately with high reproducibility without being influenced by a variation in the property of each root canal.

Figure 7:
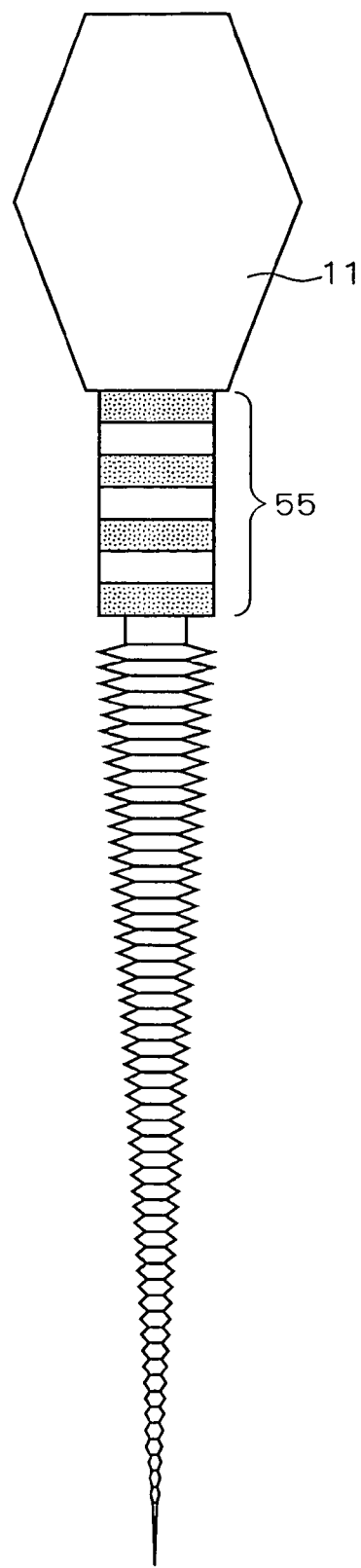
FIG. 7 is a schematic diagram illustrating a measurement electrode of the root canal length measuring apparatus according to the second embodiment of the present invention.

When the measurement electrode is pulled out from the apex, the pulling-out distance may be measured sufficiently by operator's eye measure or operator's finger, but in order to obtain a more accurate result, the measurement electrode 11 with the scale mark 55 shown in FIG. 7 or the stopper 21 with the scale mark 55 shown in FIG. 8 may be used. With the measurement electrode 11 shown in FIG. 7 and the stopper 21 shown in FIG. 8, the operator operates the measurement electrode 11 while viewing the scale mark 55 so as to be capable of acquiring the pulling-out distance of the measurement electrode 11 more accurately.

In the root canal length measuring apparatus according to the second embodiment, the position data or the display data in a root canal is stored as the reference position where a thicker root canal treatment tool is used, the reference position where a sound of a buzzer or display is changed when arriving at a specific shape of the apical constriction of root canal, or the reference position where the root canal treatment tool is operated. As a result, the accurate position in the root canal during treatment can be recognized which is difficult in the conventional technique, and control on this position is enabled.

In the root canal length measuring apparatus according to the second embodiment, in order to reduce the influence of an environmental change in the root canal and the change of the measurement electrode 11, the position data or the display data may be updated every time when the environment of the root canal changes or the measurement electrode (file) is replaced.

A cheek tooth has two or three root canals, and they are often treated collectively. In this case, position content information (numbers given to the respective root canals) is given to each root canal, and position data or display data may be stored. The position content information is not limited to information for identifying a root canal, and may include information about storage of distance from an apex, and information about storage of the apical constriction of root canal and the curved portion of a root canal. In the root canal length measuring apparatus according to the present invention, information about a root canal of another tooth of the same patient or information about another patient may be added to the position content information so as to be stored.

When the stored position data or display data is displayed on the display section 9 for each position content information, besides superimposed display, a mode is switched so that the data can be displayed. Specifically, when position data including the position content information about the apical constriction of root canal and the position data including the position content information about the curved portion of the root canal are displayed on the display section 9, as shown in FIGS. 9A and 9B, the mode is switched for each position content information so that the data is displayed. FIG. 9A typically illustrates a shape of the root canal when the display mode 56 is M1 and the apical constriction of root canal starts on the position of the storage position mark 53 according to the position content information about the apical constriction of root canal. On the other hand, FIG. 9B typically illustrates a shape of the root canal when the display mode 56 is switched into M2 by the operating switch, not shown, and the curved portion of the root canal starts on the position of the storage position mark 53 according to the position content information about the curved portion of the root canal. As a result, the operator can easily recognize what the storage position mark 53 currently displayed on the display section 9 indicates. The position data or the display data stored together with these position content information about the root canal is transmitted to a ultrasonic treatment apparatus for treating a root canal or a motor for root canal enlargement, so as to be capable of being used for control of the apparatus operation at the time of the root canal treatment.

A selecting means which can select whether or not the reference position is displayed may be provided to the display section 9. In the root canal length measuring apparatus shown in FIG. 1, the selecting means 21 is provided into the CPU 5 so as to select whether or not the reference position is displayed on the display section 9. The selecting means 21 may be provided into the display section, Third Embodiment In even some conventional root canal length measuring apparatuses, scale marks are provided to the indicator. These marks show only average values of corresponding root canal positions obtained by detecting impedance values in a lot of root canals, a ratio of the impedance values and a difference in the impedances. Specifically, an example of the conventional root canal length measuring apparatus for detecting the ratio of the impedance in a root canal is described. In the conventional root canal length measuring apparatus, when the measurement electrode 11 arrives at an apex, the ratios of the impedances in the root canal measured at a plurality of frequencies obtains approximately predetermined constant values, and indicates APEX.

In the conventional root canal length measuring apparatus, scale marks 1, 2 and 3 are given to the indicator correspondingly to the positions −1 mm, −2 mm and −3 mm as average values obtained by measuring a lot of root canals. That is to say, when the indicator swigs to the scale mark positions 1, 2 and 3, it is found that the measurement electrode 11 is present on the positions −1 mm, −2 mm and −3 mm away from the apex averagely. However, since an error in respective root canals is large, the position of the measurement electrode 11 in the root canal during measurement cannot be specified.

Specifically, a relationship between the scale marks of the indicator and the ratio of the impedances in root canals is described below. For example, the scale marks of the indicator, the distance (average value) from the apex, and the ratio of the impedances in the root canal establish a relationship shown in Table 1. In Table 1, when the ratio is 0.9, the scale mark of the indicator is 3, when the ratio is 0.85, the scale mark of the indicator is 2, and when the ratio is 0.75, the scale mark of the indicator is 1. In the conventional root canal length measuring apparatus shown in Table 1, as the measurement electrode 11 comes closer to the apex, the ratio becomes smaller.

TABLE 1

| Scale mark of the indicator | Distance from the apex | Ratio of impedances in the root canal |
|---|---|---|
| APEX | 0 mm | 0.6 |
| 1 | −1 (average value) | 0.75 |
| 2 | −2 (average value) | 0.85 |
| 3 | −3 (average value) | 0.9 |

In the conventional root canal length measuring apparatus, the ratio of the impedances in the root canal corresponding to the display dot is determined based on Table 1. The ratios of the impedances in the root canal corresponding to the display dots may be determined based on an average value obtained by actually measuring a lot of root canals, or the ratios of the impedances in root canals corresponding to the display dots may be determined by interpolation according to the relationship shown in Table 1.

FIG. 10 is a pattern diagram illustrating the indicator in the conventional root canal length measuring apparatus. On the indicator shown in FIG. 10, the ratios of the impedances in the root canal corresponding to the display dots are described for convenience of simple description. The ratios of the impedances in the root canal corresponding to the display dots are not described on the indicator of an actual root canal length measuring apparatus.

Some of the scale marks of the indicator, namely, the portion from 3 to APEX is enlarged to be displayed on the indicator shown in FIG. 10. The scale mark 3 shows the 20th display dot. The 20th display dot is turned on within a range where the ratio of the impedance in the root canal is larger than 0.89 and is 0.9 or less. The 22nd display dot shown in FIG. 10 is turned on within a range where the ratio of the impedances in the root canal is larger than 0.87 and is 0.88 or less. In the conventional root canal length measuring apparatus, the ratios of the impedances in the root canal corresponding to the display dots are predetermined, and the respective dots are turned on according to a change in the ratio in the measured impedances in the root canal.

However, in the conventional root canal length measuring apparatus, the relationship between the measurement data on the position away from the apex and the actual position greatly varies between root canals. For this reason, the actual distance from the apex to the measurement electrode 11 does not always match with the scale mark of the indicator shown in Table 1. For this reason, the scale marks of the indicator shown in FIG. 10 does not always show the distance of the measurement electrode 11 from the apex.

In the root canal length measuring apparatus according to the third embodiment, the position data or the display data at the time when the measurement electrode 11 is positioned on the predetermined distance from the apex is stored as described in the second embodiment, and the position data or the display data are used so as to rescale the scale marks of the indicator.

A relationship between the position data (in this example, the ratio of the impedance values in the root canal) stored by the method described in the second embodiment and the distance from the apex is shown in Table 2.

TABLE 2

| Distance from the apex | The ratio of the impedances in the root canal |
|---|---|
| 0 mm | 0.6 |
| −1 | 0.8 |
| −2 | 0.9 |
| −3 | 0.95 |

In the root canal length measuring apparatus according to the third embodiment, the ratios of the impedances in the root canal corresponding to the display dots on the indicator are rescaled as shown in FIG. 11. FIG. 11 is a pattern diagram illustrating the indicator of the root canal length measuring apparatus according to the third embodiment. For convenience of the simple explanation, the ratios of the impedance values in the root canal corresponding to the display dots are described on the indicator shown in FIG. 11. The ratios of the impedances in the root canal corresponding to the display dots are not described on the inductor of the actual canal root length measuring apparatus.

As to the indicator shown in FIG. 11, the portion from the scale mark 3 up to APEX on the indicator is enlarged to be shown, and the scale mark 3 shows the 20th display dot. The 20th display dot is set so as to be turned on within a range where the ratio of the impedance values in the root canal is larger than 0.94 and is 0.95 or less. The 22nd display dot shown in FIG. 11 is set so as to be turned on within a range where the ratio of the impedance in the root canal is larger than 0.92 and is 0.93 or less. In the root canal length measuring apparatus according to the third embodiment, the relationship between the display dots and the ratios of the impedances in the root canal is rescaled by using the ratios (position data) of the impedances in the root canal stored as shown in Table 2, and the setting of the scale marks is stored in the memory section. For this reason, in the root canal length measuring apparatus according to the third embodiment, when the same root canal is remeasured, the scale marks on the indicator approximately correspond to the distance from the apex to the measurement electrode.

Not shown in FIG. 11, but the correction is made on the range where the measurement electrode is −3 mm or more away from the apex (range of the scale mark 3 or more of the indicator), based on the result of Table 2, so that smooth display is enabled. The ratio of the impedance in the root canal corresponding to each display dot is changed on the indicator shown in FIG. 11 without changing the number of display dots displayed between the scale marks (for example, between the scale marks 2 and 1). The present invention is, however, not limited to this, and the number of the display dots displayed between the scale marks is changed without changing the ratio of the impedance in the root canal corresponding to each display dot, so that the scale marks of the indicator may be rescaled. It goes without saying that the scale marks of the indicator after this resealing can be stored for each patient, each tooth and each root canal.

In the root canal length measuring apparatus according to the third embodiment, the indicator just after the turning-on of the power shows values according to the relationship between the display dot shown in FIG. 10 and the ratio of the impedance in the root canal similarly to the conventional apparatus. Thereafter, when the position data on the one or more reference positions is stored, the root canal length measuring apparatus according to the third embodiment rescales the relationship between the display dots and the ratios of the impedances in the root canals based on the position data on the reference positions so that measurement thereafter is displayed. This display is used until the position data on the new reference position is stored next time.

In the root canal length measuring apparatus according to the third embodiment, since the accurate position of the measurement electrode can be displayed for each root canal to be measured and treated, the root canal treatment such as the root canal enlargement and root canal cleaning can be done safely and securely. As a result, the root canal length measuring apparatus which is easily used can be realized. Particularly this apparatus is very effective for the case where the root canal length measurement is again made on the same root canal.

In the root canal length measuring apparatus according to the third embodiment, a determination is made in advance whether the position data is stored from one reference position or two reference positions so that the process can be simplified. In the root canal length measuring apparatus according to the third embodiment, when the display of the indicator is changed into display corresponding to a root canal during the measurement, display colors are changed so that the operator easily recognize the display. Such a function may be provided.

An interpolation is made on positions other than the reference position where the data are stored like Table 2 by a simple ratio calculation on the indicator shown in FIG. 11. However, when a function where the property of the root canal is taken into consideration can be utilized, the more accurate interpolation can be made. The feeling of movement of the measurement electrode in the root canal matches with swinging of the indicator, and thus the apparatus is used more easily.

The relationship between the display dots of the indicator and the ratios of the impedances in the root canal in the root canal length measuring apparatus according to the third embodiment is described. However, the present invention is not limited to this, and thus any value which can be measured by the root canal length measuring apparatus may be used. That is to say, a relationship between the display dots of the indicator and the impedance in the root canal, the difference in the impedance in the root canal or a value obtained by combining a plurality of impedances in root canals may be used.

In the root canal length measuring apparatus according to the third embodiment, the position information about the measurement electrode can be displayed quantitatively with accuracy of substantially 1 mm within the range of −3 mm away from the apex as shown in FIG. 11. Absolute accuracy cannot be ensured, but since the four display dots shown in FIG. 11 are displayed with an interval of 1 mm, the position information about the measurement electrode can be quantitatively displayed with resolution of 0.25 mm.

In the root canal length measuring apparatus of the present invention, the present invention is not limited to the indicator shown in FIG. 11, and thus scale marks of the indicator are given to a display obtained by patterning the root canal as shown in FIG. 4A so that the position of the measurement electrode may be displayed. In another manner, the distance of the measurement electrode from the apex (unit: mm) may be display as a numerical value as shown in FIG. 12.

Fourth Embodiment

Figure 13:
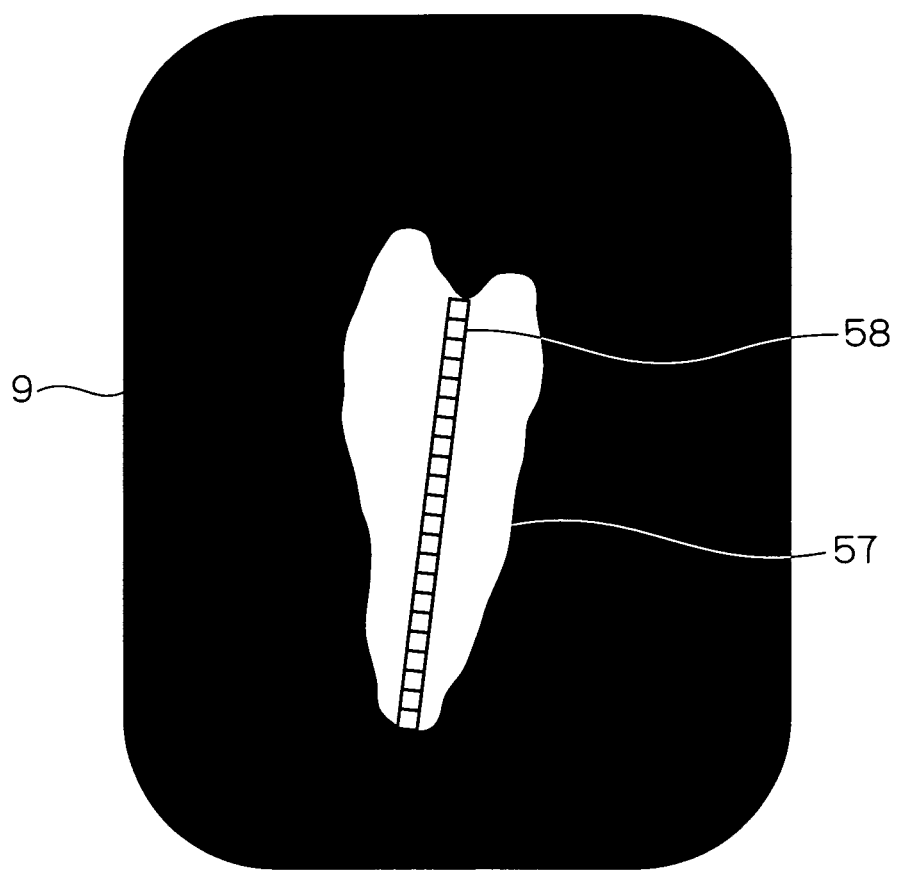
FIG. 13 is a diagram illustrating a display example of the root canal length measuring apparatus according to a fourth embodiment of the present invention.

In the third embodiment, the reference position is stored so that the distance of the measurement electrode from the apex in the root canal to be measured can be acquired. For this reason, in the root canal length measuring apparatus according to the fourth embodiment, the position of the measurement electrode is superimposed on an X-ray image of the root canal to be measured so as to be displayed as shown in FIG. 13 based on the distance of the measurement electrode from the apex acquired in the third embodiment. In FIG. 13, the X-ray image 57 and the indicator 58 are displayed in a superimposed manner on the display section 9.

An X-ray image pickup apparatus which is used for current dentistry has a function for measuring a distance to any position on the picked-up X-ray image 57 according to a process for obtaining a magnifying power of the X-ray image with respect to an actual tooth based on the distance between an X-ray sensor or a film and an X-ray generating device. Distance scale marks are easily added to the X-ray image 57 of the root canal. As described in the third embodiment, since the information about the schematic position of the measurement electrode 11 from the apex can be acquired, the schematic position information about the measurement electrode 11 is transmitted to PC on which the X-ray image 57 of the root canal to be measured is displayed via the bidirectional communication means 17 so as to be capable of being displayed in a superimposed manner.

In the root canal length measuring apparatus according to the fourth embodiment, the position of the measurement electrode 11 is displayed on the X-ray image 57 of the root canal at real time based on the schematic position information about the measurement electrode 11. When the fourth embodiment is applied to the root canal treatment apparatus where the measurement electrode 11 serves also as the root canal treatment tool, the position of the root canal treatment tool (edged tool), namely, a tip position of the file or the reamer for root canal enlargement can be displayed on the X-ray image 57 of the root canal to be measured in a superimposed manner. For this reason, in the root canal treatment apparatus, while a treatment condition is being comprehensively evaluated, the treatment can be done. That is to say, in the root canal treatment apparatus according to the fourth embodiment, while conditions of a tooth quality on a root canal enlarged portion and a thickness of a tool layer are securely understood, the treatment can be done.

Fifth Embodiment

Figure 14:
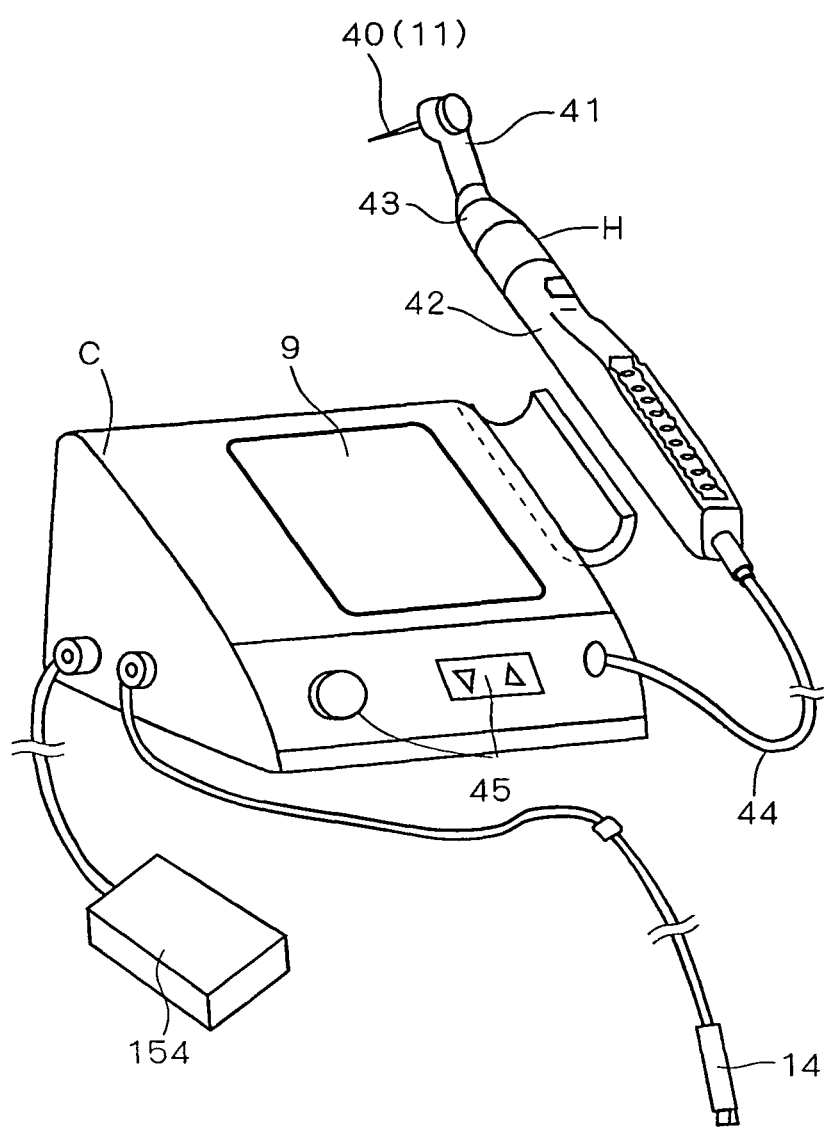
FIG. 14 is a schematic diagram illustrating a root canal treatment apparatus according to a fifth embodiment of the present invention.

The fifth embodiment refers to the root canal treatment apparatus having the function of the root canal measuring apparatus in which the root canal treatment tool serves also as the measurement electrode 11. Specifically, FIG. 14 is a schematic diagram illustrating the root canal treatment apparatus according to the fifth embodiment. The root canal treatment apparatus shown in FIG. 14 has a hand piece H and a stationary controller main body C. The hand piece H is composed of a head 41 to which the root canal treatment tool 40 serving also as the measurement electrode 11 is mounted, a hand piece main body 42 and a shank 43. The hand piece H is connected to the controller main body C via a tube 44. The hand piece main body 42 contains an electrically-driven micro-motor as a motor for driving the root canal treatment tool 40.

In the root canal treatment apparatus shown in FIG. 14, the root canal treatment tool 40 serves also as the measurement electrode 11 shown in FIG. 1, and the root canal treatment tool 40 and the oral electrode 14 can measure the root canal length described in the first to fourth embodiments. In the root canal treatment apparatus shown in FIG. 14, FIGS. 4A and 4B are displayed on the display section 9 of the controller main body C. When the switch or the foot pedal 154 provided to the operating section 45, or the operating switch provided on the hand piece H (not shown) is operated, the position data or the display data on any position of the root canal treatment tool 40 in the root canal can be stored.

When a root canal is treated in the root canal treatment apparatus, the rotation of the root canal treatment tool 40 is stopped on a predetermined position of the root canal, the rotating direction of the root canal treatment tool 40 is reversed, the regular rotation and the reverse rotation of the root canal treatment tool 40 are repeated, or the rotating speed of the root canal treatment tool 40 is slowed down. Therefore, in the root canal treatment apparatus according to the fifth embodiment, the position where the rotation of the root canal treatment tool 40 is stopped is a reference position, and the position data or the display data on the reference position is stored in advance. When the stored position data or display data on the reference position matches with the position data or the display data acquired from the root canal treatment tool 40 serving also as the measurement electrode 11, the control for stopping the rotation of the root canal treatment tool 40 is linked.

For example, position data or display data about a position −2 mm from an apex as a position where the rotating speed of the root canal treatment tool 40 is slowed down is stored as the position data or the display data on the reference position, and position data or display data about a position −1 mm away from the apex as a position where the rotation of the root canal treatment tool 40 is stopped is stored. In this case, since the rotating speed of the root canal treatment tool 40 is slowed down on the position −2 mm away from the apex and the rotation of the root canal treatment tool 40 is stopped on the position −1 mm away from the apex in the root canal treatment apparatus according to the fifth embodiment, the operator can easily treat the root canal. When the position data on the reference position is reflected in the operation control of the root canal treatment tool, the result of the root canal length measurement is not always displayed on the display section 9. Therefore, the display section 9 shows only the rotating speed and the rotating direction.

In the root canal treatment apparatus according to the fifth embodiment, the root canal treatment tool 40 is controlled in conjunction with the reference position stored in advance. This control is described with reference to the block diagram of the root canal treatment apparatus according to the fifth embodiment in FIG. 15. The root canal treatment apparatus shown in FIG. 15 basically has the same constitution in the block diagram of FIG. 1 except that a motor 61 which rotates the root canal treatment tool 40, a transistor switch 62, a driver circuit 63, a rotating direction changeover switch 64 and a load torque detecting resistor 65 are provided. For this reason, in the root canal treatment apparatus shown in FIG. 15, the components which are the same as those in the root canal length measuring apparatus shown in FIG. 1 are designated by the same reference numerals, and the detailed description thereof is omitted.

Figure 15:
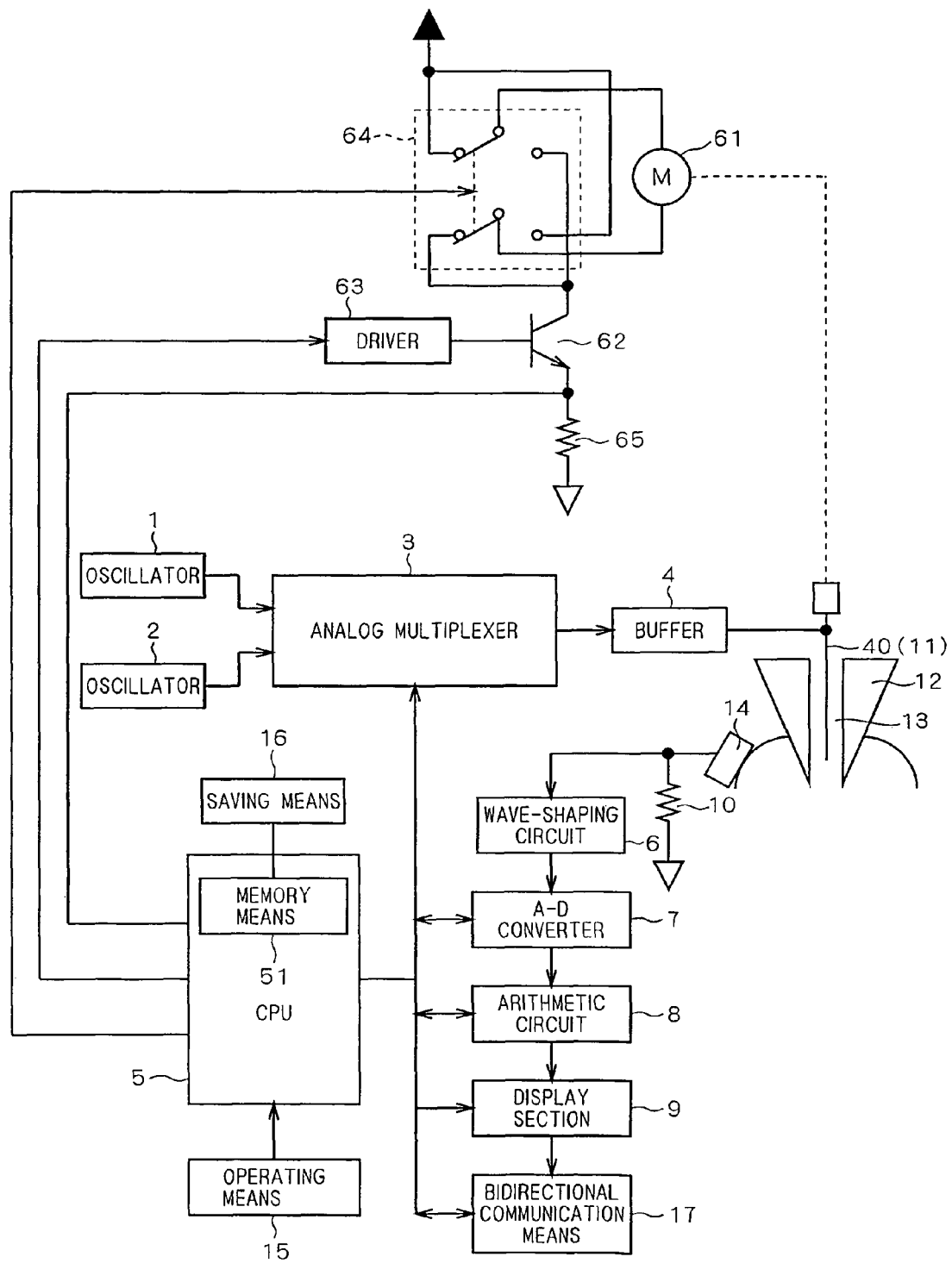
FIG. 15 is a block diagram illustrating the root canal treatment apparatus according to the fifth embodiment of the present invention.
Figure 16:
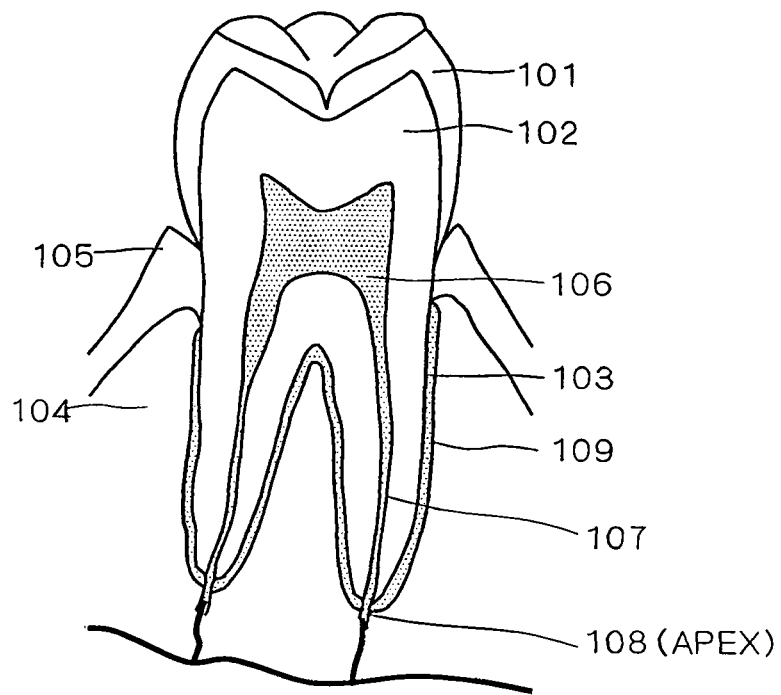
FIG. 16 is a cross-sectional view illustrating a tooth.

In the root canal treatment apparatus shown in FIG. 15, the driver circuit 63 is operated by a control signal output from the CPU 5, and the transistor switch 62 is turned on/off so as to drive the motor 61. In the root canal treatment apparatus shown in FIG. 15, the rotating direction changeover switch 64 changes over the rotating direction of the motor 61. In the root canal treatment apparatus shown in FIG. 15, a voltage generated in the load torque detecting resistor 65 by an electric current of the motor 61 is supplied to the CPU 5, so that a load torque is detected. That is to say, in the root canal treatment apparatus shown in FIG. 15, when the position data or the display data on the reference position stored in the memory means 51 matches with the position data or the display data acquired from the root canal treatment tool 40 serving also as the measurement electrode 11, the CPU 5 supplies a predetermined control signal to the driver circuit 63 and the rotating direction changeover switch 64 so as to control the rotation of the root canal treatment tool 40.

Details of the linkage between the root canal length measurement and the root canal treatment tool 40 are disclosed in Japanese Patent Publication No. 3264607. Details of the control and the constitution of the root canal treatment tool 40 are disclosed in Japanese Patent Publication No. 3223042 and Japanese Patent Application Laid-Open No. 2003-19970. The above describes the root canal length measuring apparatus and the root canal treatment apparatus of the present invention, but these root canal length measuring apparatus and root canal treatment apparatus can be mounted to a dental treatment table (dental treatment unit) having a turbine hand piece for cutting and abrading a tooth, a motor hand piece, and a scaler. The mounting here may be external connection via a connector, or may be containing in the treatment table. The dental treatment table (dental treatment unit) normally includes an operating means which is represented by a foot switch for operating various treatment tools, a display section which shows states of the treatment tools and the treatment table or displays a patient's oral image, and a driving section which drives the treatment tools and the treatment table. Therefore, when the root canal length measuring apparatus or the root canal treatment apparatus of the present invention is mounted to the dental treatment table, the operating means, the display section and the driving section can be used as some of the components of the root canal length measuring apparatus or the root canal treatment apparatus of the present invention.

While the invention has been shown and described in detail, the foregoing description is in all aspects illustrative and not restrictive. It is therefore understood that numerous modifications and variations can be devised without departing from the scope of the invention.

What is claimed is:
1. A root canal length measuring apparatus comprising:
a measurement electrode which is configured to be inserted into a root canal;
an oral electrode which is configured to be held in an oral cavity;

a measuring section which applies an electric measuring signal between said measurement electrode and said oral electrode and specifies an apex position so as to measure a root canal length;

a memory means configured to store a reference position in the root canal other than said apex position in response to an input by an operator made at a time that a tip of the measurement electrode reaches the reference position; and a display section which displays said reference position.

2. The root canal length measuring apparatus according to claim 1, wherein said reference position is used as position information at a time of root canal enlargement.

3. The root canal length measuring apparatus according to claim 1, wherein said measurement electrode on a position of said apex is pulled up by a predetermined distance, and said reference position stored in said memory means on said position is used as distance information of said measurement electrode from said apex.

4. The root canal length measuring apparatus according to claim 3, wherein distance of said measurement electrode from said apex is displayed on said display section based on said reference position.

5. The root canal length measuring apparatus according to claim 3, further comprising a display information arithmetic means for automatically rescaling a scale of said display section based on said reference position.

6. The root canal length measuring apparatus according to claim 4, wherein said display section superimposes to display the distance of said measurement electrode from said apex on an X-ray image of said root canal to be measured.

7. The root canal length measuring apparatus according to claim 1, further comprising a selecting means for selecting whether or not said reference position is displayed on said display section.

8. The root canal length measuring apparatus according to claim 1, wherein the memory means stores, in addition to said reference position, position content information corresponding to said reference position to be stored in relation with said reference position.

9. The root canal length measuring apparatus according to claim 1, further comprising a saving means which saves said reference position stored in said memory means.

10. The root canal length measuring apparatus according to claim 9, wherein said saving means saves said reference position stored in said memory means as well as in a management means, and reads said reference position saved based on said management means.

11. The root canal length measuring apparatus according to claim 1, further comprising a communication means which transmits said reference position stored in said memory means to outside.

12. The root canal length measuring apparatus according to claim 1, wherein said input by the operator comprises operation of one of a foot pedal, a button and a microphone.

13. A root canal treatment apparatus, comprising:

a root canal length measuring apparatus having a measurement electrode configured for being inserted into a root canal, an oral electrode configured for being held in an oral cavity, a measuring section for applying an electric measuring signal between said measurement electrode and said oral electrode and for specifying an apex position for measuring a root canal length, a memory means for storing a reference position in the root canal other than the apex position in response to an input by an operator made at a time that a tip of the measurement electrode reaches the reference position;

a root canal treatment tool which is configured to treat a root canal;

a driving section which drives said root canal treatment tool; and a control section which controls said driving section based on said reference position stored in said memory means; and a display section which displays said reference position; and wherein said measurement electrode works as said root canal treatment tool.

14. The root canal treatment apparatus according to claim 13, wherein said control section controls said driving section so that a driving force is changed at said reference position.

15. The root canal treatment apparatus according to claim 13, wherein said driving section is any one of an electric motor and an air motor and drives to rotate said root canal treatment tool, said control section controls said driving section so that at least any one of a rotating force and a rotating direction is changed at said reference position.

16. A root canal length measuring apparatus comprising:

a measurement electrode which is configured to be inserted into a root canal;

an oral electrode, which is configured to be held in an oral cavity;

a measuring section which applies an electric measuring signal between said measurement electrode and said oral electrode and specifies an apex position so as to measure a root canal length;

a memory means configured to store a reference position in said root canal other than that of the apex position in response to an input by an operator made at a time that a tip of the measurement electrode reaches the reference position;

and a display section which displays said reference position; and wherein said apex position is determined using at least one of an impedance value of the root canal, a difference in the impedance value of the root canal during said procedure and a ratio of said difference in said impedance value and said impedance value of said root canal.

17. The root canal length measuring apparatus according to claim 1, wherein the reference position is one of an apical constriction, a curved portion of the root canal, a step, a ledge, a location of pathologic changes, and a particular distance from the apex position for reference during root canal enlargement.

18. The root canal length measuring apparatus according to claim 1, wherein the reference position is displayed on the display section as a storage position mark or as a display dot.

* * * * *